US009011314B2

(12) United States Patent
Davis et al.

(10) Patent No.: US 9,011,314 B2
(45) Date of Patent: Apr. 21, 2015

(54) SYSTEM AND METHOD FOR IMPLANTING A CATHETER

(75) Inventors: Phillip J Davis, West Gardiner, ME (US); Thomas W Winegar, Hawthorne, NJ (US); Harvey D Homan, Basking Ridge, NJ (US); Andrew R Leopold, Hawthorn, IL (US)

(73) Assignee: Ingenion Medical Limited, London (GB)

(*) Notice: Subject to any disclaimer, the term of this patent is extended or adjusted under 35 U.S.C. 154(b) by 1274 days.

(21) Appl. No.: 11/993,356

(22) PCT Filed: Nov. 30, 2007

(86) PCT No.: PCT/US2007/086157
§ 371 (c)(1),
(2), (4) Date: Jul. 23, 2008

(87) PCT Pub. No.: WO2006/067557
PCT Pub. Date: Jun. 5, 2008

(65) Prior Publication Data
US 2009/0157053 A1 Jun. 18, 2009

Related U.S. Application Data

(60) Provisional application No. 60/861,803, filed on Nov. 30, 2006.

(51) Int. Cl.
*A61F 2/00* (2006.01)
*A61M 25/01* (2006.01)

(52) U.S. Cl.
CPC ..................................... *A61M 25/01* (2013.01)

(58) Field of Classification Search
USPC ........... 600/30, 40, 587, 591; 604/530, 96.01; 606/1, 119, 139, 144, 232
See application file for complete search history.

(56) References Cited

U.S. PATENT DOCUMENTS 3,108,595 A * 10/1963 Overment ...................... 604/105
3,241,554 A * 3/1966 Coanda ......................... 604/105
(Continued)

FOREIGN PATENT DOCUMENTS

JP 2002-520087 7/2002
WO WO-01/56629 A2 8/2001

*Primary Examiner* — Scott Medway
(74) *Attorney, Agent, or Firm* — Stephen J. Lieb; Frommer Lawrence & Haug LLP

(57) ABSTRACT

A system for implanting a catheter in a urethra. The system includes a catheter having a valve disposed at a distal portion of the catheter. The valve may be operable in response to an external magnetic field. The system also includes a tool having a tip member extending into an opening at the distal portion of the catheter to couple the tool to the catheter. the system also includes an element extending from the tool. The catheter has an internal path that provides a conduit for the element to be extended through the valve to engage a proximal portion of the catheter. The tool is adapted use the element to stress the catheter and stiffen the catheter along the length of the catheter. Stiffening the catheter facilitates implantation of the catheter in the urethra by enabling pull forces, push forces, and torque forces to be transmitted from the tool through the catheter to the proximal portion of the catheter without undue stress on the urethra. The element is extendible and retractable to position the catheter between stressed and relaxed states while maintaining engagement to the catheter proximal portion. The tool, element and tip member are removable from the catheter after implantation of the catheter in the urethra.

23 Claims, 12 Drawing Sheets

(56) References Cited

U.S. PATENT DOCUMENTS

| | | | |
|---|---|---|---|
| 3,706,307 A * | 12/1972 | Hasson | 600/591 |
| 4,016,867 A * | 4/1977 | King et al. | 600/591 |
| 4,204,548 A * | 5/1980 | Kurz | 600/591 |
| 4,224,951 A * | 9/1980 | Hasson | 600/591 |
| 4,489,732 A | 12/1984 | Hasson | |
| 5,030,199 A | 7/1991 | Barwick et al. | |
| 5,234,409 A * | 8/1993 | Goldberg et al. | 604/99.04 |
| 5,248,302 A | 9/1993 | Patrick et al. | |
| 5,318,578 A * | 6/1994 | Hasson | 606/139 |
| 5,352,182 A | 10/1994 | Kalb et al. | |
| 5,409,453 A * | 4/1995 | Lundquist et al. | 604/22 |
| 5,509,889 A | 4/1996 | Kalb et al. | |
| 5,601,537 A | 2/1997 | Frassica | |
| 5,730,704 A * | 3/1998 | Avitall | 600/374 |
| 5,749,826 A | 5/1998 | Faulkner | |
| 5,971,975 A * | 10/1999 | Mills et al. | 604/527 |
| 5,976,068 A | 11/1999 | Hakky et al. | |
| 6,045,536 A * | 4/2000 | Meier et al. | 604/174 |
| 6,050,934 A | 4/2000 | Mikhail et al. | |
| 6,066,088 A | 5/2000 | Davis | |
| 6,325,790 B1 * | 12/2001 | Trotta | 604/523 |
| 7,070,587 B2 * | 7/2006 | Meier et al. | 604/533 |
| 8,083,692 B2 * | 12/2011 | Mangiardi et al. | 600/587 |
| 2002/0087148 A1 * | 7/2002 | Brock et al. | 606/1 |
| 2002/0188299 A1 * | 12/2002 | Reiley et al. | 606/79 |
| 2003/0216759 A1 * | 11/2003 | Burbank et al. | 606/157 |
| 2005/0148999 A1 | 7/2005 | Beaufore et al. | |
| 2008/0287862 A1 * | 11/2008 | Weitzner et al. | 604/28 |
| 2010/0063437 A1 * | 3/2010 | Nelson et al. | 604/35 |
| 2010/0161042 A1 * | 6/2010 | Maisano et al. | 623/2.11 |

* cited by examiner

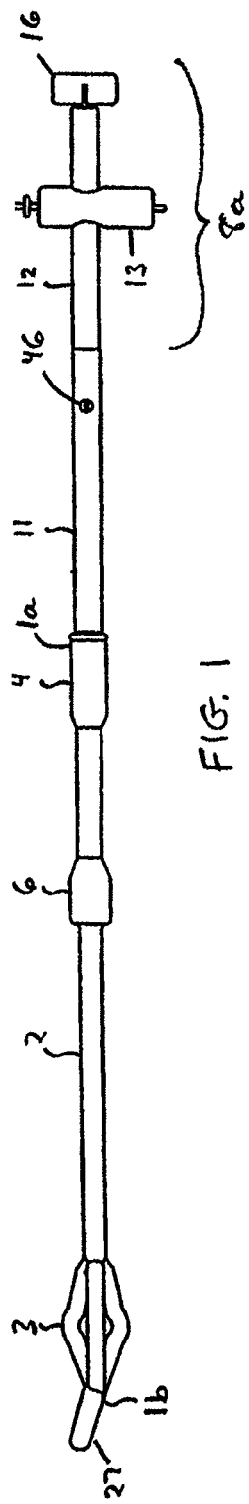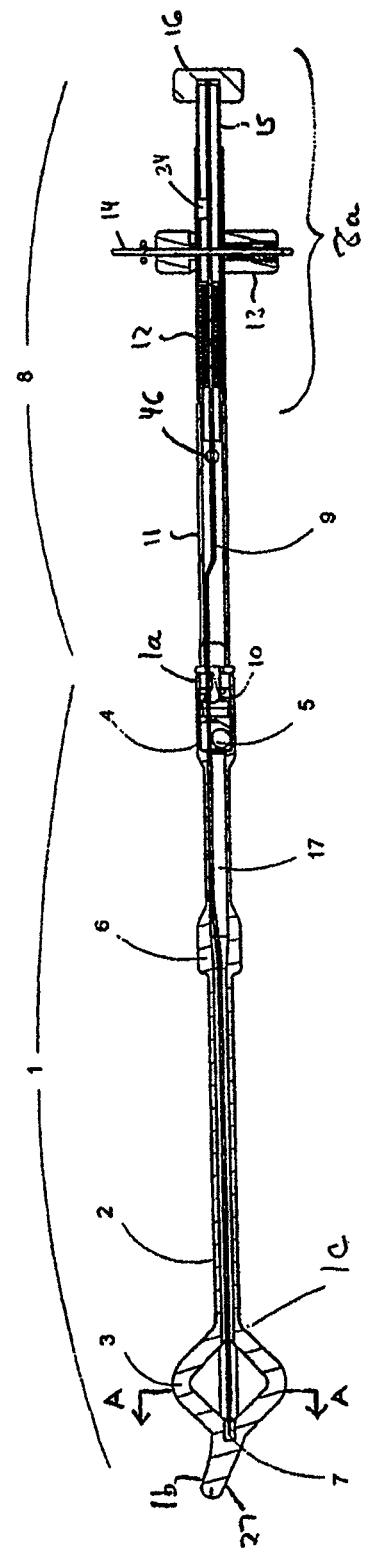

Figure 5
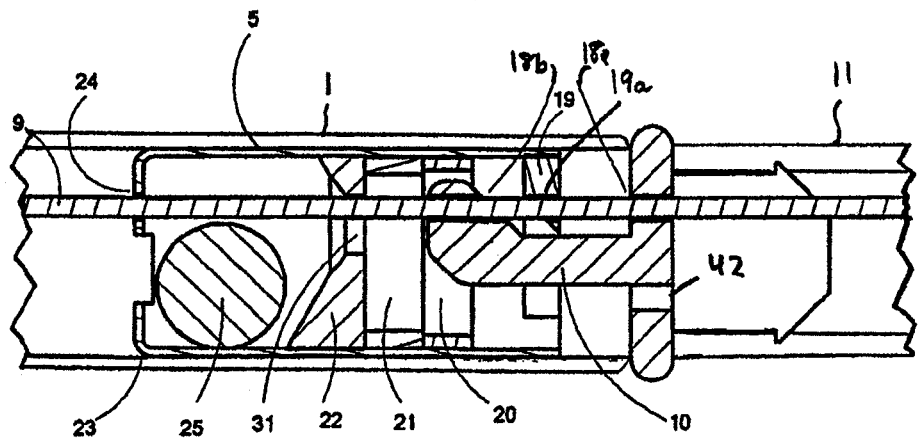
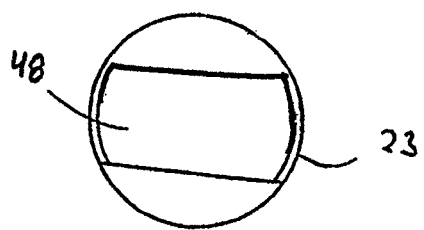
FIG. 5A
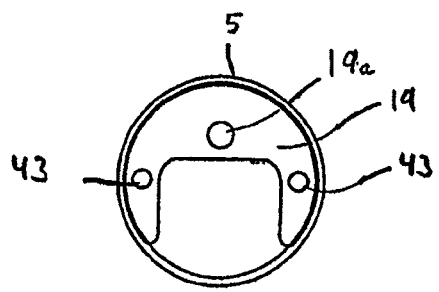
FIG. 5C
FIG. 5B

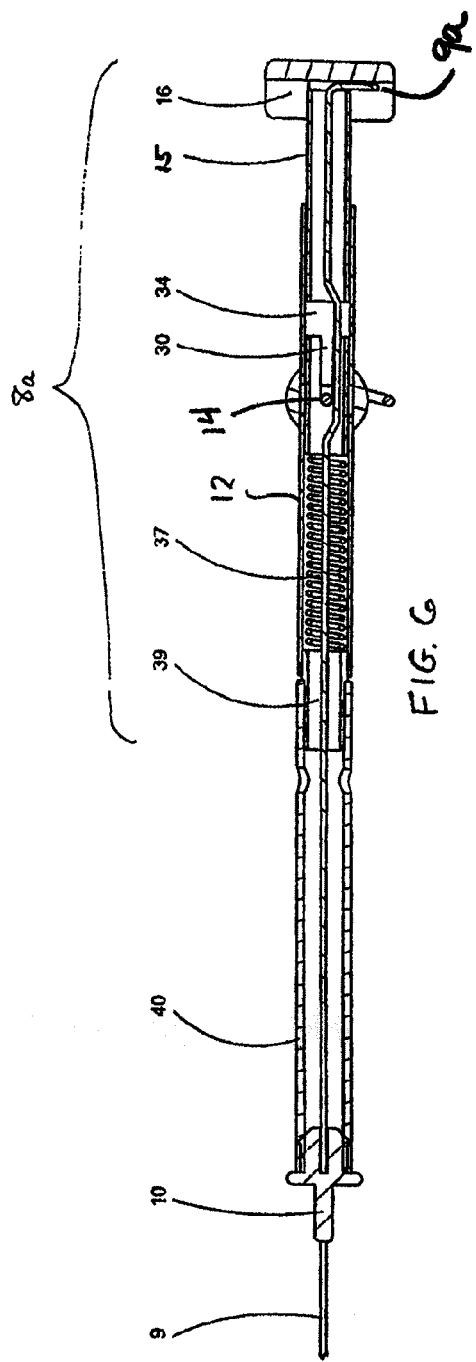
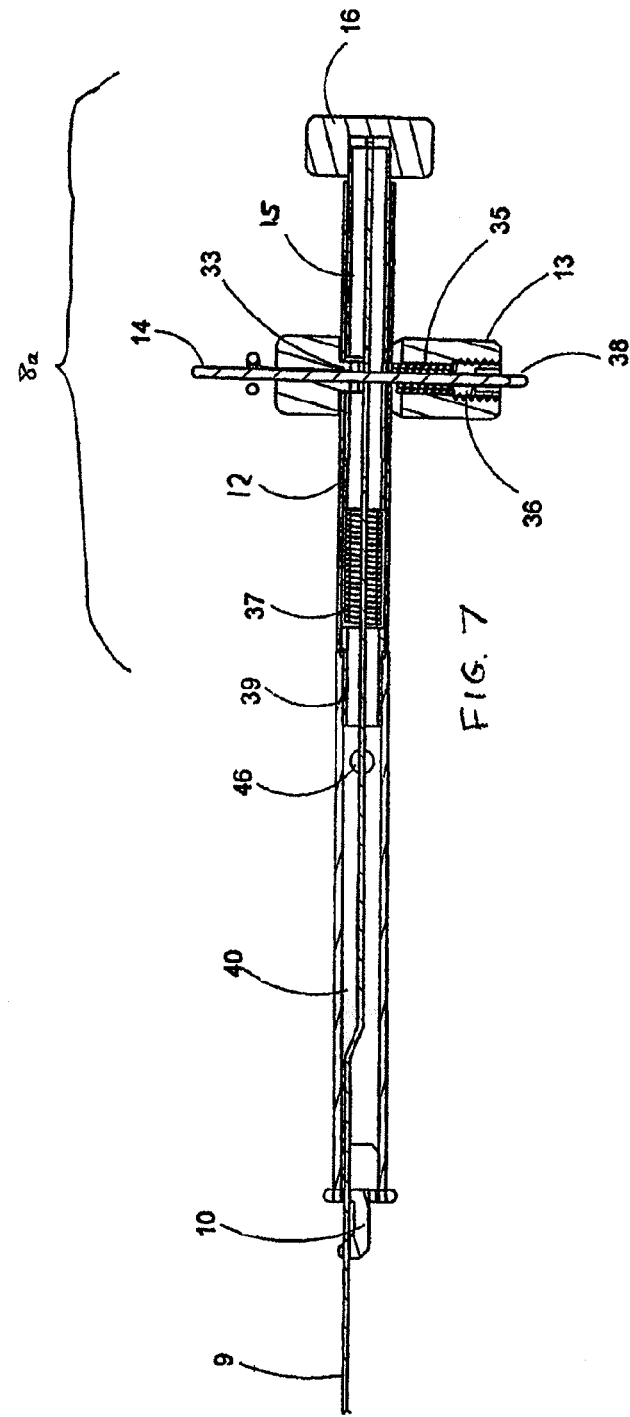

SYSTEM AND METHOD FOR IMPLANTING A CATHETER

BACKGROUND

1. Field of the Invention

The present invention relates generally to a system and method for implanting a catheter, such as a catheter having a magnetic valve (a valved catheter), in a tubular cavity or hollow organ. In particular, the present invention relates to a system and method that utilizes an insertion tool suitable for implanting a catheter, for example, in the urethra.

2. Background of the Invention

There are conventional devices for inserting and removing intraurethral sphincter prostheses and/or catheters for treatment of urinary retention deficiencies using devices for detecting, gripping and positioning valves and stents within the urethra. There are also conventional devices that use multi-lumen devices for inflating and deflating stent and/or catheter fixating balloons. There are separate tools for insertion and extraction, and tethers for retrieval of valves and stents.

Unfortunately, implanting and removing intraurethral devices are complex operations and do not provide immediate confirmation of proper placement of the devices in the urethra. Such immediate confirmation is desirable to avoid possible patient complications due to misplacement, or additional procedures to replace the prosthesis. Further, the tool when pushing the catheter may cause the catheter to buckle as a result of the flexible nature of the catheter.

Therefore, it would be an advancement in the state of the art to provide an improved catheter and a system and method that facilitates insertion of a catheter and/or a stent into a patient's urethra.

SUMMARY

Accordingly, the present invention relates to an improved system and method for implanting a catheter using an insertion tool that may allow push, pull, and torque to be transmitted from the tool internally through a catheter lumen or channel, and push, pull, and torque to be transmitted through a catheter wall from a distal portion of the catheter to a proximal portion to facilitate location and placement of the catheter in a tubular cavity or hollow organ, thereby enabling the catheter to be implanted.

One embodiment of the present invention is directed to a system for inserting a catheter ("the system"). The system includes a catheter, tool and a mechanism. The catheter has a proximal portion and a distal portion. The catheter also has a valve disposed within an internal lumen or channel. The tool has a tip member and an extendible element that extends through the tip member, the valve, and the internal channel to the proximal portion of the catheter. The element may be a wire, a tube, a wire within a tube, or any other suitable structure and cross section capable of translating torque and axial forces (push and pull). The element is releasably attached to a portion of the catheter. The tip member couples the tool to the catheter such that the element extends through the tip member and through the internal channel towards the proximal portion of the catheter.

The mechanism is mounted on the tool to apply extending and retracting forces to the element and may be any mechanism known in the art to be capable of applying an axial force. Such known mechanisms include, but are not limited to, for example, push buttons, cams, threaded devices that lock to one another and advance and/or retract when twisted, rotary interlocking members, spring loaded pins, geared devices, slides, ratchets, and motors.

Another embodiment of the present invention is directed to a system for inserting a catheter which includes a catheter having a proximal portion, a distal portion, an internal channel or lumen, a valve disposed within the channel, and a tool having a tool tip, an extendible element with an internal passageway, and a locking filament disposed for slidable movement within the internal passageway and may extend beyond the proximal and distal portions of the extendible element. Alternatively, the filament may not extend beyond the proximal and distal portions of the extendible element. The locking filament may be a fine thread, fiber or wire, single strand, multi-strand, or spun, of a suitable material. The catheter has a socket tip in the proximal portion which is adapted to accept the extendible element and the locking filament to releasably lock the extendible element to the socket tip. By locking the extendible element to the socket tip, the extendible element can impart push, pull and torque forces at the proximal end of the catheter. The tool tip is adapted to allow passage of the extendible element through aligned holes in the tool tip and the valve, thereby locking the tool tip to the valve. The tool tip thus locked to the valve can impart push, pull, and torque to the distal portion of the catheter.

Another embodiment ensures the extendible element remains in the socket of the catheter until intentionally removed by providing a constant proximally directed force to the extendible element. This can be achieved by placing a biasing device, such as, for example, an extension spring, in the mechanism that urges the extendible element proximally when the tool is coupled to the catheter. The biasing device places the catheter in a tensionally stressed condition. Any elongation of the catheter will be compensated for by the biasing device, thus maintaining placement of the extendible element in the socket.

Another embodiment locks the tool tip to the catheter by passing the extendible element through at least two aligned holes in the tool tip and at least one hole in the catheter placed in alignment with the holes in the tool tip.

Another embodiment of the present invention is the system in which the element is in a stressed state, and the catheter is in a stressed state, when the mechanism extends the element. The element is constructed of a material and cross section suitable to withstand encountered axial tensile and compressive forces and resulting stresses without distorting or buckling.

Yet another embodiment of the present invention is the system wherein the element is in a relaxed state when the mechanism retracts the element.

Yet another embodiment of the present invention is the system in which the tool is adapted to apply a rotation to the catheter by applying a torsional force to the proximal portion of the catheter and to the distal portion of the catheter.

Yet another embodiment of the present invention is the system in which the tool is adapted to apply a push force to the proximal portion of the catheter and to the distal portion of the catheter.

Yet another embodiment of the present invention is the system wherein the tool is adapted to apply a pull force to the catheter by applying a tensional force to the distal portion of the catheter.

Yet another embodiment of the present invention is the system wherein the tool comprises a locking mechanism to positively and releasably lock the extendible element to a distal portion of the catheter thus permitting a pull force to be applied to the distal portion of the catheter.

Yet another embodiment of the present invention is the system wherein the valve is operable in response to an external magnetic field.

Yet another embodiment of the present invention is the system wherein said valve includes a housing, a valve seat assembly sealingly attached to the housing and having an aperture. The valve also includes a spherical magnetic valve element disposed for universal movement within the housing, an inlet end for entrance of fluid, and an outlet end for exit of fluid. The outlet end having an opening for the tip member of the tool.

Yet another embodiment of the present invention is the system wherein the element has a proximal portion, which is adapted for releasable engagement to the proximal portion of the catheter.

Yet another embodiment of the present invention is the system wherein the mechanism maintains a biasing force to urge the extendible element proximally in the catheter to maintain engagement of the proximal end of the extendible element with the proximal portion of the catheter.

Yet another embodiment of the present invention is the system wherein the tool further comprises means for moving said element between a first position in which the element extends through the catheter without applied stress and a second position to apply stress to the catheter.

Yet another embodiment of the present invention is the system wherein the tool further comprises means for releasably locking the element in at least each of the first and second positions.

Yet another embodiment of the present invention is the system wherein the tool is enabled to apply and transmit one or more of push, pull, or torque through the catheter during insertion.

Yet another embodiment of the present invention is the system wherein the means for releasably locking the element when released enables the element to be removed from the catheter, and said tip member being removable from said catheter when the element is removed from extending through the member.

Yet another embodiment of the present invention is the system wherein the torsional force applied to the proximal portion of the catheter is simultaneously applied and substantially equal in magnitude and direction to the torsional force applied to the distal portion of the catheter.

Yet another embodiment of the present invention is the system wherein the push force applied to the proximal portion of the catheter is simultaneously applied and substantially equal in magnitude and direction to the push force applied to the distal portion of the catheter.

Yet another embodiment of the present invention is the system wherein the extendible element holds the valve in an open position.

Yet another embodiment of the present invention is the system that also includes a first opening in the valve, a first opening in the tool tip, that aligns with the first opening in the valve. There may also be a second opening in the tool tip aligns with the first opening in the valve, and an extendible element that passes from the first opening in the tool tip through the first opening in the valve and through the second opening in the tool tip, thereby locking the tool tip and the valve together.

Yet another embodiment of the present invention is the system wherein the extendible element has an outer diameter of between approximately 0.01 inches and 0.20 inches.

Yet another embodiment of the present invention is the system wherein the locking filament has an outer diameter of between approximately 0.002 inches and 0.020 inches.

Yet another embodiment of the present invention is the system further including an expandable member that is inserted with the catheter and expands to form a seal surrounding a portion of the catheter.

Yet another embodiment of the present invention is the system wherein a proximal portion of the catheter is fabricated from a material having a first durometer and a distal portion of the catheter is fabricated from a material having a second durometer, the first durometer being lower than the second durometer.

BRIEF DESCRIPTION OF THE DRAWINGS

Embodiments of the invention will become more apparent from a reading of the following description in connection with the accompanying drawings, in which:

FIG. 1 is a side view of a catheter and insertion tool locked together and in a stressed state ready for implantation;

FIG. 2 is a sectional view of the catheter and insertion tool of FIG. 1 in a relaxed state;

FIG. 5 is a more detailed view of FIG. 2 showing the coupling of the catheter and the insertion tool using the tool tip member and extendible element;

FIGS. 5A and 5B is a distally directed view of two embodiments of the end of the valve housing, as shown in FIG. 5;

FIG. 5C is proximally directed view of the c-ring of the valve;

FIG. 6 is a sectional view of the insertion tool with the extendible element retracted to illustrate the latching mechanism of the tool in a relaxed state in which the view is rotated 90 degrees from the view shown in FIG. 3;

FIG. 7 is a sectional view of the insertion tool of FIG. 3 with the extendible element extending from the tool advanced to illustrate a tensioning mechanism of the tool in a stressed state in which the view is rotated 90 degrees from the sectional view shown in FIG. 6;

DETAILED DESCRIPTION

Figure 3:
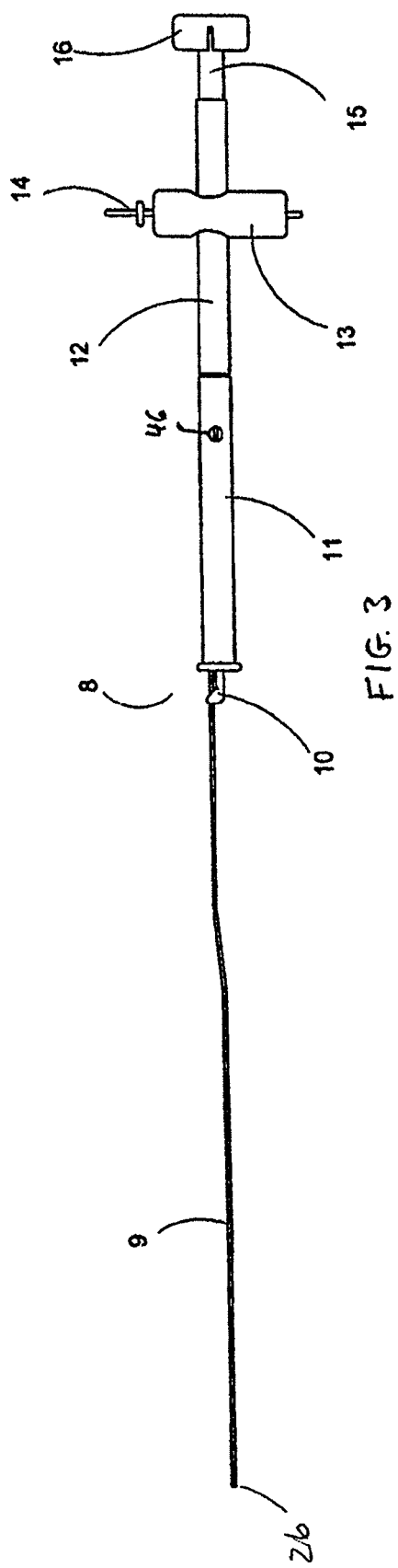
FIG. 3 is a side view of the insertion tool of FIGS. 1 and 2 with the catheter removed and the extendible element extending from the tool retracted to illustrate the relaxed state of the tool.

As used herein, the term "lumen" will be understood to be an inner open space of a tubular cavity or organ and shall be used interchangeably with "channel" throughout the specification. As used herein, the term "valve" will be understood to include magnetically operated valves, other remotely operated valves or manually operated valves suitable for placement within a catheter. As used herein, the anchoring device referred to by the term "malecot" should be understood to include pigtail, balloons, spines, umbrellas, or other configurations of known devices for anchoring catheters placed in hollow organs. For illustrative purposes only, the catheter is described in the specification in terms of a urethral catheter with the understanding that this is one of many potential applications for the instant invention. One skilled in the art will recognize that the catheter disclosed may be used in other applications in which a catheter would be beneficial.

Generally, the present invention is directed to a catheter having an essentially cylindrical shaped body, a proximal portion, a distal portion, and at least one internal path between the proximal portion and the distal portion. For example, when a magnetic valve is used, the valve may be positioned in the catheter and the valve operable in response to an external magnetic field. A tool has a tip member that may extend from the tool into an opening at the distal end of the catheter and adapted to engage the distal end of the valve. Alternatively, the tool tip member may be flat and not extend into the distal end of the catheter, wherein the extendible element may lock directly to the proximal portion of the catheter.

When engaged with the distal end of the valve, the tool tip couples the tool to the catheter. In an alternate embodiment, the tool can be coupled to the catheter directly. An element extends from the tool, through the tool tip, the valve, and along the internal path between proximal portion and the distal portion of the catheter to the proximal portion of the catheter. By extending the element, the tool is capable of stressing the catheter to stiffen it along its length to facilitate implantation of the catheter in a tubular cavity or hollow organ.

Implantation is facilitated because the element extending through the stressed catheter enables at least push and torque to be transmitted from the tool through the catheter, via the extendible element, to the proximal portion of the catheter, while push, pull, and torque are delivered to the catheter distal portion, via the tool tip member, and transmitted through the catheter wall to its proximal portion. The element also adds rigidity in the catheter to ease implantation. Optionally, the proximal catheter end may further have a channel for passage of an optional guide wire or filament also intended for ease of implantation. The valve may have a cylindrical housing, a valve seat assembly attached, via a seal, in the housing having an aperture. A valve element, such as for example, a spherical valve element, may be disposed for universal movement within the housing. An inlet at one end of the housing permits entrance of fluid, and an outlet end of the housing provides for exit of fluid and has an opening for receiving the tool tip member into a cavity of the housing. The inlet end and outlet end have openings to provide a pathway for the element, and between such ends the element is extendible through the valve seat aperture and the tool tip member when the tool tip is located in the cavity of the valve housing. The functioning of the valve will be described below.

The proximal end of the catheter has a cage of loops (called herein a malecot) having at the distal end of the malecot the opening to the lumen of the flexible catheter extending to the catheter distal valve, and having at the proximal end of the malecot a tip with a socket for engagement of the end of the element having passed through such valve and lumen. The loops of the malecot may be comprised of a plurality of straight or curvilinear segments joined to the cylindrical body of the catheter at the distal portion of the malecot. At the proximal end of the malecot, the segments may be joined to form a generally cylindrical or conical structure. Between the proximal end and the distal end of the catheter, the malecot segments naturally form a structure concentric with the catheter that extends beyond the cylindrical shape of the catheter. The proximal end of the catheter may also include, for example, a pigtail, a balloon, spines or umbrella or other suitable configuration.

Located on the proximal portion of a catheter can be a sealing apparatus to sealingly abut against surrounding tissue. The sealing apparatus may have one or both of an outwardly compliant sealing element or an axially compliant sealing element around the outer perimeter. The sealing apparatus works to ensure that all fluid from a hollow organ, for instance the bladder, is directed through the lumen of the catheter. When the catheter is sealed off, for example with a valve, this apparatus will reduce bladder leakage due to conditions such as urinary incontinence.

When the distal portion of the catheter is coupled to the tool tip and the extendible element is engaged with the malecot proximal end, axial displacement of the extendible element in the proximal direction will stress the catheter and the malecot, placing them both in tension. Sufficient tension will stretch the catheter and the malecot, deforming both the catheter and the malecot. For example, a tensile stress applied axially to the cylindrical body portion of the catheter will cause the catheter to stretch proportionally to the applied stress. By application of Hooke's Law, one of ordinary skill in the art will recognize that the catheter will also deform radially, under the same axial stress, by decreasing in diameter. Likewise the malecot will deform under an axial stress. The malecot loops will first lengthen and deflect inward, the diameter of the malecot approaching that of the catheter body. Further axial stress applied to the malecot will cause the malecot to lengthen and decrease in diameter.

In some applications, distortion of the catheter under an axial load may be undesirable while the elongation and decreased diameter of the malecot may be desirable, for instance to reduce trauma to the structure receiving the catheter. In other applications, it may be desirable to have the catheter deform, but the malecot retain its natural shape. Accordingly, the malecot may be made of a resilient material having elastic properties different than those of the catheter body. For instance, to deform the malecot with little effect on the shape of the catheter body, the malecot may be made from a resilient material that deforms under a lower stress than the catheter. One of ordinary skill in the art will recognize the more easily deformed resilient material as one having a lower durometer, or a greater Poisson's ratio, than the more difficult to deform resilient material. Conversely, if it is desirable that the catheter deform under an axial stress while the malecot retains its natural shape, the catheter may be fabricated from a lower durometer material than the malecot. In either situation, it is desirable that the malecot and the catheter return to their natural configuration upon removal of the applied stress.

Magnetically operated valves exist in the art, see, for example, U.S. Pat. No. 6,066,088 (the '088 patent), which is hereby incorporated by reference in its entirety. As in the '088 patent, the valve of the instant invention comprises a cylindrical housing with proximal and distal ends, a valve seat of material sealingly attached to the distal end of the housing, and a magnetic valve element contained within the housing and a retaining device at the proximal end of the housing. The material may be for example stainless steel or other suitable material having desired properties. The valve is normally closed due to a magnetic attraction between a valve element and the spherical valve element. Upon introduction of an external magnetic force, the spherical element may be displaced from the valve seat, opening the valve. Surfaces of the valve components may be treated or coated partially or completely according to various methods to improve valve function. Coatings and surface treatments may improve, for example, the sealing characteristics, the flow characteristics, or compatibility of the valve components.

It is an embodiment of the instant invention to have the centerline of a valve seat aperture parallel to but displaced from the centerline of a cylindrical housing. By displacing the centerline, the spherical valve element may be restrained from closing the valve by passing an extendible element the valve seat in the valve. Guide holes retain the extendible element in proper alignment parallel to the valve centerline preventing jamming against the spherical valve element. In some instances it is desirable to maintain the valve in an open position during insertion of the catheter, for instance, in situations in which the initiation of flow may be used to indicate proper placement of the catheter.

Further, the housing distal end is extended to form a cavity with a c-ring terminal end. The cavity and the c-ring receive the tip member of the insertion tool which is locked to the valve by passage of the element through holes in both the tool tip member and the c-ring. The instant valve thus is configured to operate in conjunction with a tool to impart push, pull, and torque to the catheter through at least the valve. An alternate embodiment coupling the tool directly to the catheter allows push, pull, and torque to be imparted directly to the catheter.

When locked to the catheter, the extendible element is extendible and retractable to provide a stressed state and an unstressed or relaxed state, respectively, in the catheter and the element, while retaining the extendible element in engagement with the catheter at the catheter proximal portion. A tensioning mechanism is provided at the tool to move the element between such states and may releasably lock the element at each of the stressed and unstressed states. A pretension means may be provided in the tensioning mechanism that can be removed allowing the extendible element and insertion tool to be removed upon successful implantation of the valved catheter. In the stressed state, the insertion tool can provide push, pull and torque through the catheter distal end to the catheter proximal end and at least push and torque at the proximal end.

The pretension means advance proximally the extendible element a distance sufficient to engage the proximal tip of the extendible element and stress the catheter a predetermined amount by advancing the extendible element an additional distance. The pretension may be achieved by actuating the pretension means once the tool is coupled to the catheter. In another embodiment, the pretension is achieved when the tool is coupled to the catheter because of the pretension means within the tool.

In the relaxed state, intended for long term storage with the tool locked to the catheter, the element may be held under low stress in the catheter tip socket. On operation of an actuator of the tensioning mechanism, the element is advanced to its stressed state to apply additional stress on the catheter tip causing the malecot or other anchoring means to narrow for easy insertion. The element is chosen to add appropriate flexural rigidity to the catheter for easy guidance and control. The tensioning mechanism has a device that locks the element in the elevated stress position. When the implanting physician believes that the catheter's proximal end, i.e., malecot, is successfully placed, for instance in the bladder, actuating the device releases the tool to the low stress state causing the catheter's proximal malecot to enlarge (extending the malecot loops outward from their stressed inward or narrow position) without disengaging the tool. The physician may then pull back gently on the tool for tactile confirmation where, in the example of a urethral catheter, the enlarged malecot will impinge on the bladder neck. On placement confirmation the physician may then unclasp and remove the locking device for the extendible element allowing extraction of the element. Removal of the element disengages the tool tip member from the valve and permits extraction of the insertion tool from the catheter, leaving the catheter and valve implanted. The functions of the extendible element locking device are to maintain minimum stress on the element so that the element cannot escape engagement with the catheters proximal tip and to prevent premature disengagement of catheter and insertion tool. Premature release of the extendible element from the catheter tip could cause puncture of the receiving structure, which could include, in the example of a urethral catheter, the urethra or bladder. Premature disengagement of catheter and insertion tool may also cause implantation failure.

By coupling both the proximal and distal ends of the catheter to the tool, the user is able to impart push, pull, and torque that are essentially equal in magnitude and direction to both ends of the catheter, aiding insertion. In another embodiment, the proximal tip of the extendible member is alternatively biased toward the socket via a biasing means, such as a spring, to prevent premature release.

The insertion tool of the present design adds no bulk to the catheter during implantation as it is concentric to the catheter but smaller diameter and as the extendible element passes through the valve and up the lumen of the catheter to the proximal portion. Thus inserting the instant catheter will be less traumatic to surrounding tissue than by distally pushing the valved catheter with enlarged malecot as is the current practice. The catheter is also less bulky and rigid than if a pushing wire had extended external of said catheter and valve to the catheter's proximal end.

The invention is useful in that the tool, when coupled to the catheter, may provide the transmission of one or more of push, pull and torque from the tool through the catheter to its proximal end to facilitate implantation and proper placement of such catheter in the urethra without undue stress on the urethra, in the example of a urethral catheter, in which the tool stiffens the otherwise flexible catheter along its length to facilitate such placement. After placement the tool relaxes the catheter to enable capture of its proximal end prior to removal of the catheter, for example, for a urethral catheter, the proximal portion is captured in the bladder prior to removal of the tool from the catheter and the urethra. The valve of the catheter once inserted into the urethra selectively provides fluid discharge there from in response to activation of the valve.

Referring to FIGS. 1 and 2, a valved catheter 1 is shown coupled to the insertion tool 8. The valved catheter 1 comprises flexible catheter body 2 having a distal end 1a with a bulge 4 holding a magnetic proximity valve 5, and a proximal end 1b having a malecot 3 and a socket 7 at the catheter proximal tip 27 adjacent one end of the malecot, a lumen 17 defined by the catheter interior wall extending from such valve 5 and opening to the gap at the distal end 1c of the malecot 3 between the loops providing the malecot, and an intermediate bulge 6. The insertion tool 8 comprises an extendible element 9 that extends through catheter 1 via lumen 17 and valve 5 to engage socket 7, a tip member 10 which couples or locks tool 8 to the catheter 1, and a tensioning mechanism 8a for advancing and retracting the element and releasably locking the element in at least one position of such advanced or retracted states to provide stressed and relaxed states, respectively, to catheter 1. Such tensioning mechanism may have a catheter segment 11, a latch body 12, a plunger 13, a pretension means 14, an inner latch 15, and push button 16, and a biasing device 62 (FIG. 15), and will be described later is more detail.

The catheter 1 is fabricated from a flexible, resilient, preferably biocompatible material through any manufacturing method known to the art. In the relaxed stress state as shown in FIG. 2, the malecot 3 is expanded to the configuration it will attain if placed in a suitably sized hollow organ. This expanded configuration makes the diameter of the malecot 3 significantly greater than the diameter of the catheter body 2.

The insertion tool 8 has at least two stable states including a latched state (malecot 3 stressed) and unlatched state (malecot 3 unstressed). The catheter 1 is shown stressed in FIG. 1 and unstressed in FIG. 2. Although shown straight, the catheter body 2 is of flexible biocompatible material, such as from molded thermoplastic, or other flexible polymeric material, and can flex along with extendible element 9 as needed during implantation, for example, in the urethra. The insertion tool 8 and catheter 1 are shown as separate components in FIGS. 3 and 4, respectively. The tool 8 components, such as extendible element 9 and tip member 10, may be made of titanium, stainless steel, plastic, or other suitable material.

Referring to FIGS. 5, 5A, 5B, 5C, and 10, extendible element 9 passes through hole 18a in valve engagement tip member 10 and continues through c-ring 19 guide hole 19a in valve 5. Extendible element 9 then continues through hole 18b in tool tip member 10 (FIG. 10) locking c-ring 19 to the tip member. Thus locked in engagement with the catheter, the tool via tool tip member 10 can provide push, pull and torque to the valved catheter 1 distal portion transmitted through c-ring 19 and lumen 17 walls to the proximal portion. Extendible element 9 continues through valve ferromagnetic ring 20, spacer ring 21, valve seat 22, aperture 31 and proximal end of the valve housing 23. In one embodiment, the proximal end of the valve housing 23 includes proximal guide hole 24 (FIG. 5A). In an alternate embodiment, valve 5 proximal end is illustrated in FIG. 5B in which case the extendible element 9 passes through slot 48. By transit through valve 5, extendible element 9 displaces spherical magnetic valve element 25 from seat 22 causing the valve to be held open and able to pass liquid during implantation. Guide hole 19a orients extendible element 9 approximately straight and parallel to valve housing 23 centerline during implantation regardless of catheter flexure caused by compliance with anatomical bends and implantation forces. By holding this segment of extendible element 9 straight as it passes through the valve 5, friction between extendible element 9 and housing 23 is minimized during extraction of extendible element 9 after implantation. Holding this segment of extendible element 9 straight and parallel to housing 23 centerline also prevents jamming of extendible element 9 against valve element 25 which would prevent extraction of extendible element 9. Extendible element 9 continues within catheter 2 lumen 17 and engages socket 7 of the catheter's proximal tip. Displacing the valve seat aperture 31 from the valve centerline permits passage of the extendible element 9 through the valve 5 without additional fluid sealing elements and permits the largest possible aperture to housing diameter ratio thus producing a valve with the lowest possible drag. Valve housing 23, valve seat 22, c-ring 19, and spacer 21, are made of nonmagnetic biocompatible material and may be at least partially coated to enhance the sealing performance or the fluid flow characteristics of the valve 5.

Figure 8:
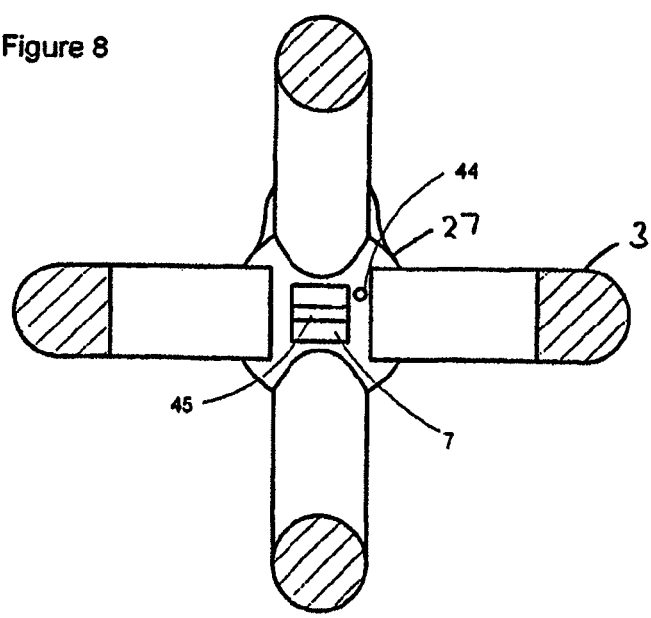
FIG. 8 is a sectional view of the catheter proximal end along line A-A of FIG. 2 without the extendible element extending from the tool to show the socket and optional guide wire hole.
Figure 9:
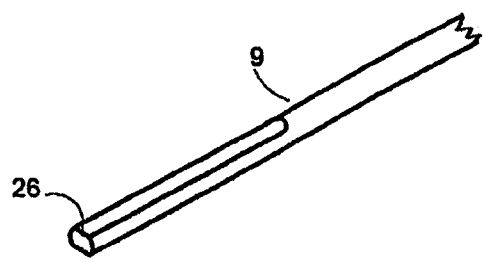
FIG. 9 is a broken perspective view of the distal portion of the extendible element extending from the tool locatable in the socket of FIG. 8.
Figure 10:
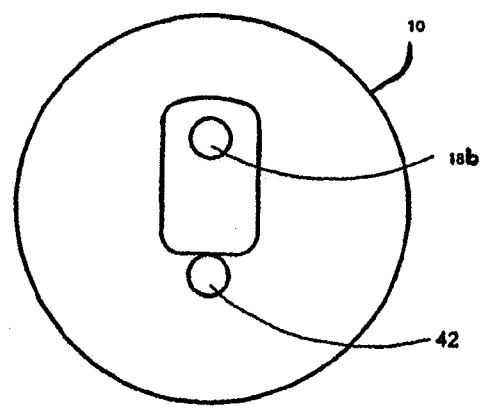
FIG. 10 is an end view of the insertion tool tip member.

Referring to FIGS. 8 and 9, in one embodiment, socket 7 has a rectangular slot 45 to receive the proximal end of extendible element 9 approximately rectangular tip 26. The approximately rectangular tip 26 is provided by flats ground on extendible element's proximal end 26 sized to fit in the slotted fitting 45. Tip 26 can thus provide torque and push to catheter proximal end 1b transmitted through socket 7. Pull on catheter proximal end 1b (shown in FIG. 2) is provided through insertion tool tip member 10 and transmitted through valve 5 and catheter body 2. In one embodiment, a biasing device 62, (shown in FIG. 15) such as an extension spring, is provided to bias the extendible element proximally to ensure the proximal tip 26 of extendible element 9 remains engaged in the socket 7. The biasing device 62 is configured to extend under a force. Thus, if the catheter becomes frictionally bound and tension is applied to the tool, the spring will extend to maintain engagement of the proximal element tip in the socket 7. Consequently, torque and push can be directly applied to the proximal portion of the catheter while pull is applied to the distal portion through the tool tip and translated to the proximal portion through the catheter body. Torque, push and pull on catheter proximal tip 27 are all useful for successful implantation.

Figure 11:
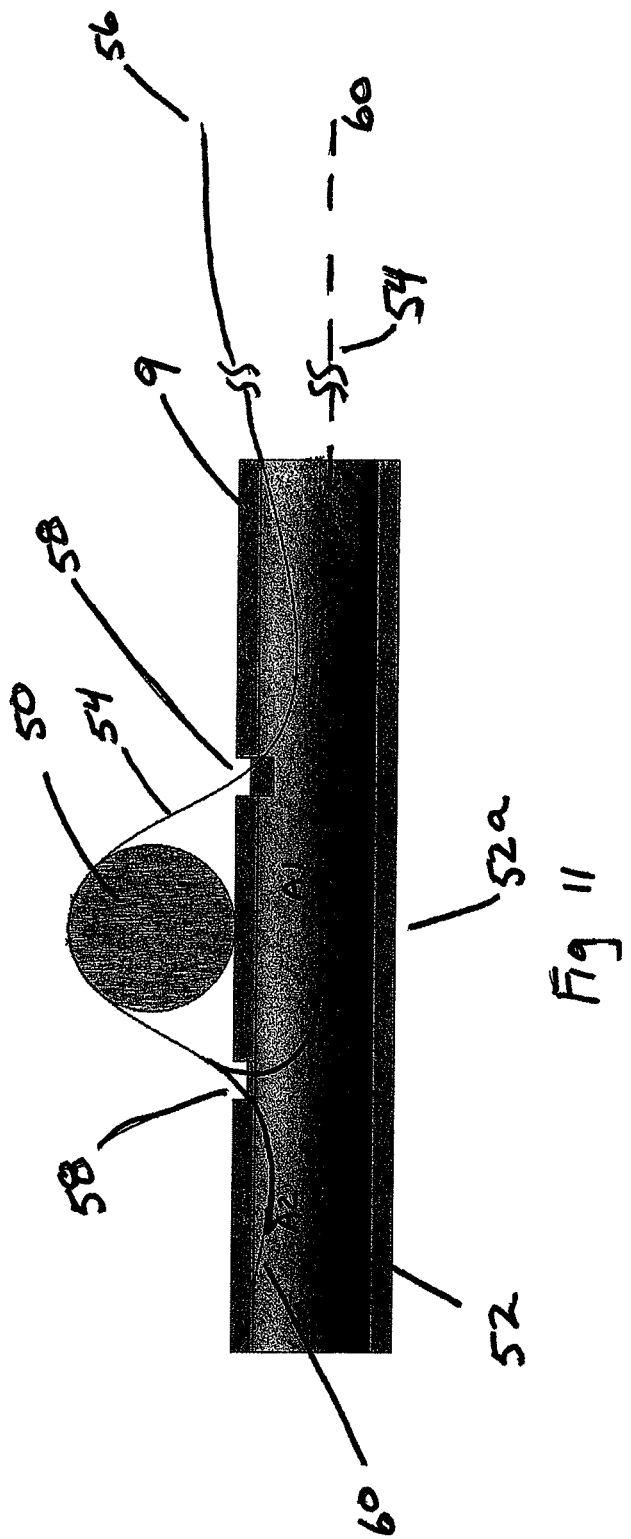
FIG. 11 is an enlarged broken sectional view of a locking mechanism.

In an alternate embodiment shown in FIG. 11, a cavity located in the proximal tip of the catheter 1 has a engageable member 50. Extendible element 9 has an internal channel 52 extending from the distal portion of the extendible element to the proximal portion of the extendible element in which locking filament 54 is slidably disposed. Locking element 54 has a first end 56 (shown broken in FIG. 11) which extends beyond the distal end of the extendible element. Internal channel 52 proximal end 52a is in open communication with the environment through at least one opening 58. A second end 60 of locking filament 54 exits internal channel 52 through opening 58, engages engageable member 50 and is returned to the internal channel 52 through one or more openings 58 in the direction according to arrow A1 or A2. In one embodiment, the locking filament 54 is sufficiently rigid so as to resist unintentional separation of the second end 60 from the internal channel 52 once the filament 54 has been re-introduced to the channel 52. In an alternate embodiment, the second end 60 of the locking filament 54 re-enters the internal channel 52 of the extendible element 9 and continues distally according to arrow A1, exiting the channel at the distal portion of the extendible element, shown as broken and dashed line 54 with second end 60. Either recited embodiment locks the proximal portion of the extendible element 9 to the socket 7 thereby allowing push, pull and torque to be applied to the proximal end tip of the catheter 27.

Figure 12:
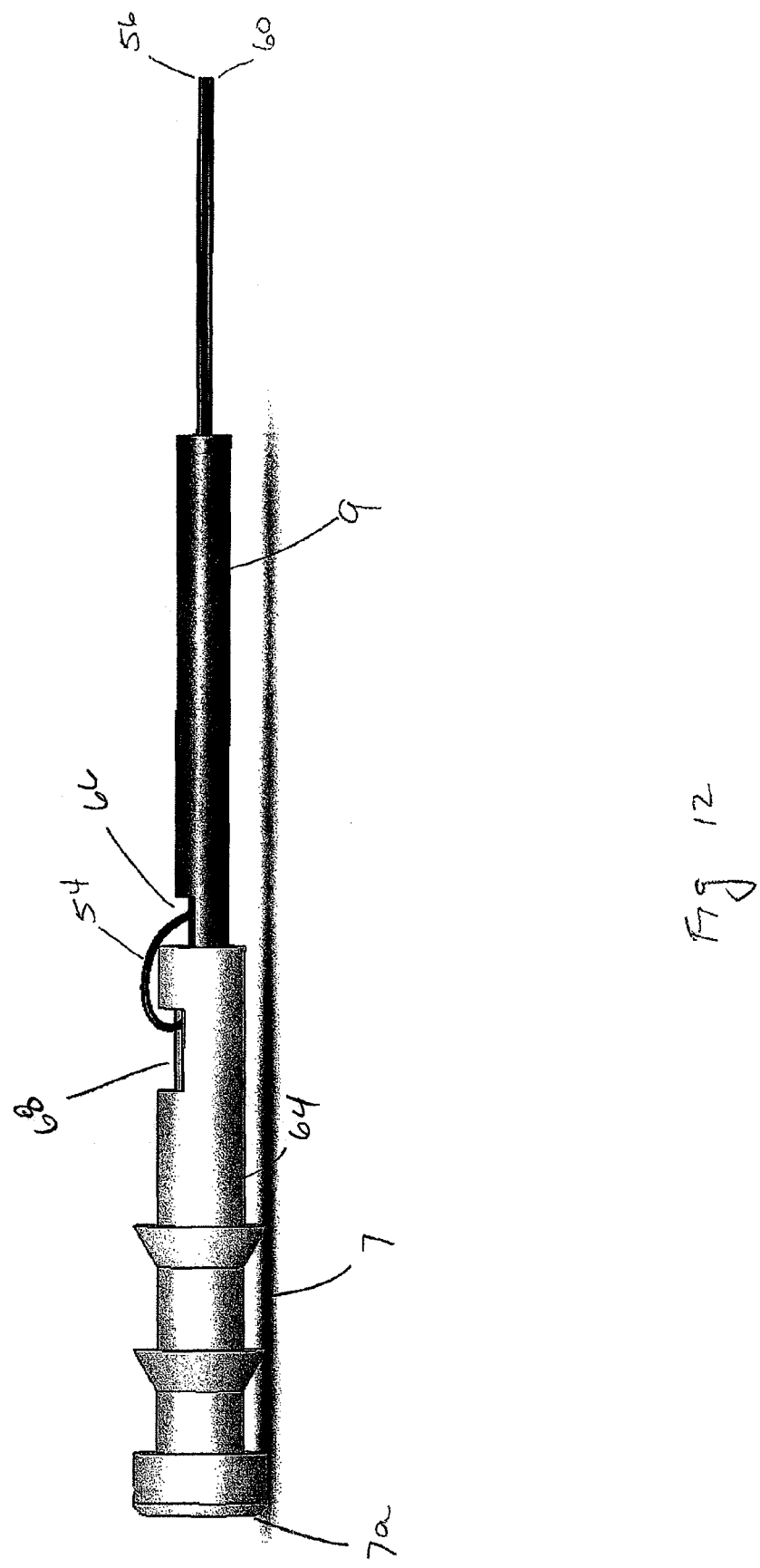
FIG. 12 shows an example of a locking wire.
Figure 13:
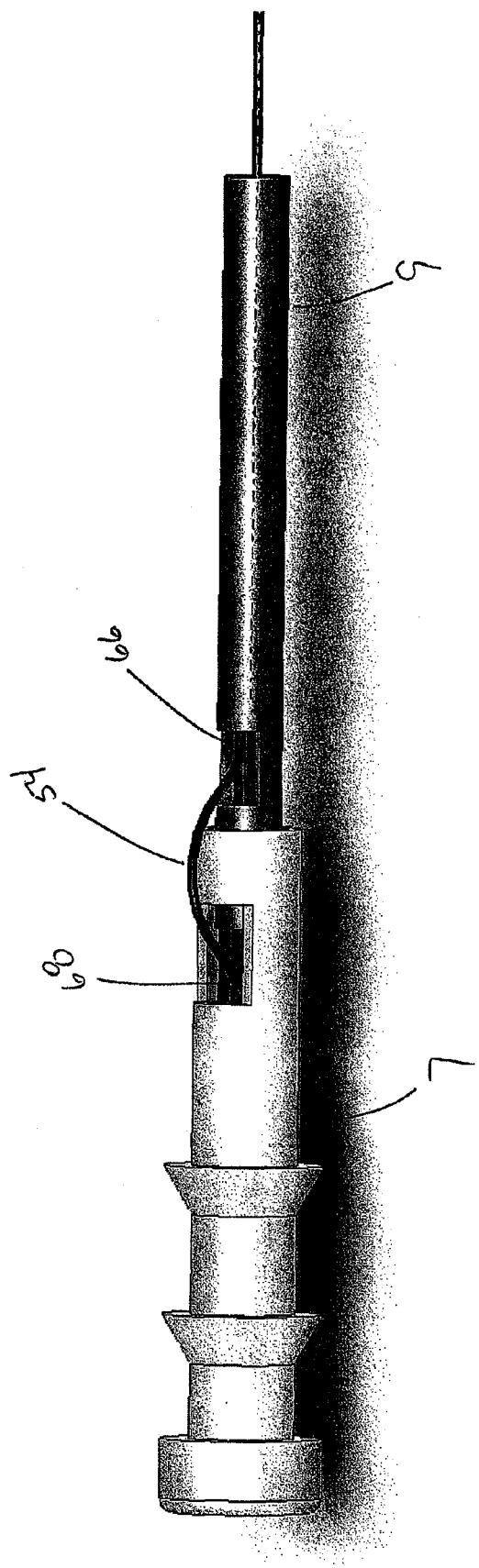
FIG. 13 shows a second example of a locking wire.
Figure 14:
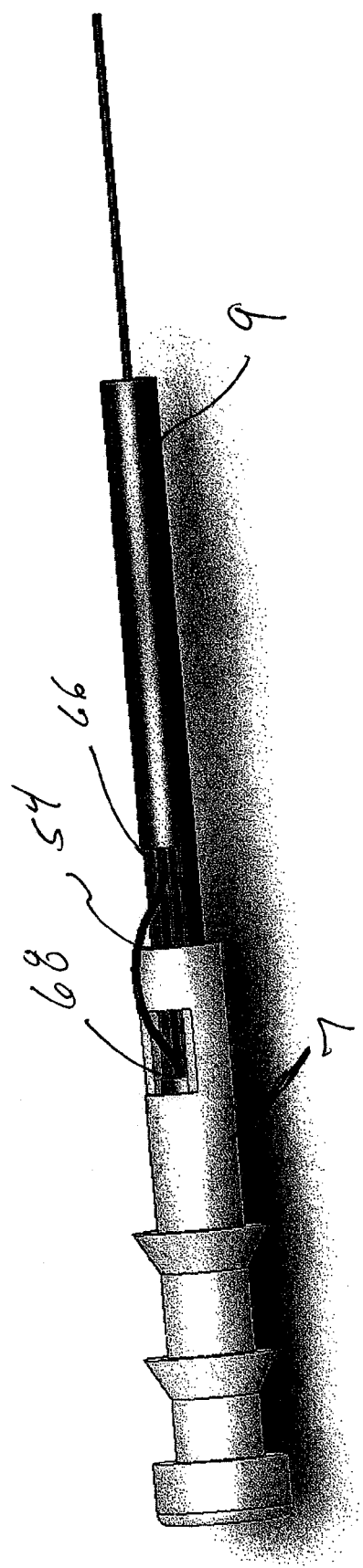
FIG. 14 shows a third example of a locking mechanism.

Further embodiments of a socket 7 and locking filament 54 are shown in FIGS. 12 and 13 in which socket 7 has at least one opening 68 through its outer surface 64 and inner surface (not shown). In FIG. 12, extendible element 9 has at least one opening 66 to at least partially align with the at least one socket opening 68. Locking filament 54 is slidably disposed in internal channel 52 of extendible element 9. In one embodiment, one end 60 of locking filament 54 exits the extendible element 9 through opening 66 outside of socket 7, re-enters internal channel 52 of extendible element 9 through the at least one socket hole 68 and the at least one opening 66 in extendible element 9. End 60 is directed distally within internal channel 52 to distal end of extendible element 9.

Another embodiment, similar to that of FIG. 12 is shown in FIG. 13 in which extendible element 9 has at least one opening 66 to at least partially align with the at least one socket opening 68. Locking filament 54 is slidably disposed in internal channel 52 of extendible element 9. One end 60 (not shown in FIG. 13) of locking filament 54 exits the extendible element 9 through opening 66 outside of socket 7, re-enters internal channel 52 of extendible element 9 through the at least one socket hole 68 and the at least one opening 66 in extendible element 9. End 60 is directed proximally within internal channel 52 to a proximal portion of extendible element 9, where frictional forces or mechanical entrapment hold the locking filament within the internal channel.

Socket 7 may further prevent the proximate end of extendible element 9 from puncturing catheter proximal end tip 27 when stressed for implantation as shown in FIG. 1. The socket 7 may be made from a puncture-resistant material to prevent the extendible element 9 from puncturing the catheter end tip 27 upon application of a compressive axial force on the extendible element 9 to impart a push to the catheter tip 27. The socket tip 7 may also have a proximal end 7*a*, best shown in FIG. 12, having a projected surface area which is from about 2.25 to 3 times the projected area of the end surface of the extendible element 9 to distribute the compressive force and prevent puncture. During implantation the malecot 3 is stretched and narrowed, as shown in FIG. 1, to reduce trauma to surrounding tissue.

Referring to FIGS. 6 and 7, compressive stress on extendible element 9 is maintained at a minimal level for long term device storage by a pretension means 14 and slight elastic stretching of catheter body 2 as transmitted through socket 7. This is the relaxed state as shown in FIG. 6. Pretension means 14 limits the motion of extendible element 9 by constraining inner latch 29 to the travel defined by slot 30. Extendible element 9 is secured to inner latch 29 by push button 16. Although pretension means 14 is shown as a latch and slot to maintain extendible wire 9 in an extended position, any known method to maintain an extensive force on extendible element 9, thereby imparting a minimal stretch to the catheter, could be employed. Such means could be push buttons, cams, gears, threaded devices, motors, ball and detent devices and the like.

The stressed state of the catheter is shown in FIG. 1 and the tool 8 is configured to apply stress to the catheter 2 in FIG. 7. To stretch catheter malecot 3, in one embodiment push button 16 is advanced until plunger 13 detent 33 engages inner latch 15 slot 34 under the influence of compressive spring 35. Spring 35 is retained in plunger 13 and prestressed by socket screw 36 which is hollowed along its centerline for passage of pretension means 14. Compression spring 37 returns push button 16 and inner latch 15 to the relaxed state when finger pressure is applied to plunger 13 spring end 38 releases inner latch 15 slot 34 from detent 33. When the implanting physician believes that the malecot structure 3 is in the proper location, which, for example would be in the bladder for a urethral catheter, the tool is returned to the relaxed state and pulled gently. In this state, the expanded malecot structure 3 gives the physician tactile confirmation of contact with the bladder neck, in the case of a urethral catheter, and assurance of proper catheter placement. Adapter 39 adapts insertion tool catheter segment 40 to inserter latch body 12 compression spring 37. Insertion tool catheter segment 40 connects insertion tool tip 10 to the latch mechanism in a length appropriate for the intended application of the catheter 1. It is shown at an arbitrary length for ease of illustration. In practice, for example in the case of a urethral catheter, the catheter segment 40 is made just long enough to hold the latch mechanism 8*a* outside the body. As such, mechanism 8*a* provides a handle for the physician to manually position or manipulate the catheter 1 through the tool 8. Additional confirmation of proper placement may be provided by fluid flow as extendible element 9 holds the valve open and fluid contained in the target location may pass through the lumen 17 and the valve 5. Although mechanism 8*a* is described, other handles having a movable element, such as button 16 or any other extension device known to the art, coupled to extendible element 9, to extend and retract the extendible element 9 between stressed and relaxed catheter states may also be used in tool 8.

On successful implantation, the insertion tool 8 is disconnected from the valved catheter 1 and removed (pulled) without displacing the implanted catheter. To perform this, push button 16 is released to the relaxed state. Pretension means 14 is opened and extracted from plunger 13. Extendible element 9, inner latch 15 and push button 16 are extracted by pulling on pushbutton 16. Removal of extendible element 9 unlocks tool tip 10 from C-ring 19 allowing tool tip 10 and valve 5 to decouple and tool 8 to be extracted from the distal portion of the catheter.

Upon successful implantation of a catheter employing a locking filament 54, removal of the insertion tool is similar to the process described above. With the extendible element 9 extended and the catheter 1 in a stressed state, an end 56 of locking filament 54 is grasped at the distal end of the extendible element 9*b*. Applying a distally directed tension force to the filament 54 to overcome the resistive forces created between the filament 54, the internal channel 52, and the socket 7 will withdraw the locking filament 54 from engagement with the socket 7. Once the locking filament 54 is disengaged from the socket 7, the proximal end 26 of extendible element 9 is free to be removed from the socket 7. Push button 16 is released to the relaxed state. Pretension means 14 is opened and extracted from plunger 13. Extendible element 9, inner latch 15 and push button 16 are extracted by pulling on pushbutton 16. Removal of extendible element 9 unlocks tool tip 10 from C-ring 19 allowing tool tip 10 and valve 5 to decouple and tool 8 to be extracted from the distal portion of the catheter 1.

Referring to FIG. 5A, slot 48 in the proximal end of valve housing 23 provides an inlet aperture which cannot be completely obstructed by the spherical valve element 25 regardless of valve element 25 rest position. Guide hole 24 may be present in one embodiment to guide extendible element 9 through the valve 5 and maintain the extendible guide element 9 parallel to the centerline of the valve 5. This inlet aperture rectangular slot 48 eliminates the possibility of the inlet being plugged by the spherical valve element. As shown in FIG. 5*b*, slot 48 may be enlarged to increase fluid flow and reduce fluid drag. Also in valve 5, spacer ring 21 (FIG. 5) may be provided between valve seat 22 and ferromagnetic attractive ring 20. This ring 21 may be constructed in multiple lengths to permit adjustment of valve closure forces by altering the spacing between ferromagnetic attractive ring 20 and spherical magnetic valve element 25 when valve 5 is assembled. Also, in valve 5, the holes 43 (FIG. 5C) of c-ring 19 may optionally be provided as anchoring points for optional sutures or tethers (not shown) used to extract the valved catheter 1.

Referring to FIG. 8, an optional hole (or channel) 44 passes the length of the catheter proximal tip 27 and provides a passage for a standard guide wire (not shown) that the implanting physician may optionally use to ease difficult implantations.

Figure 15:
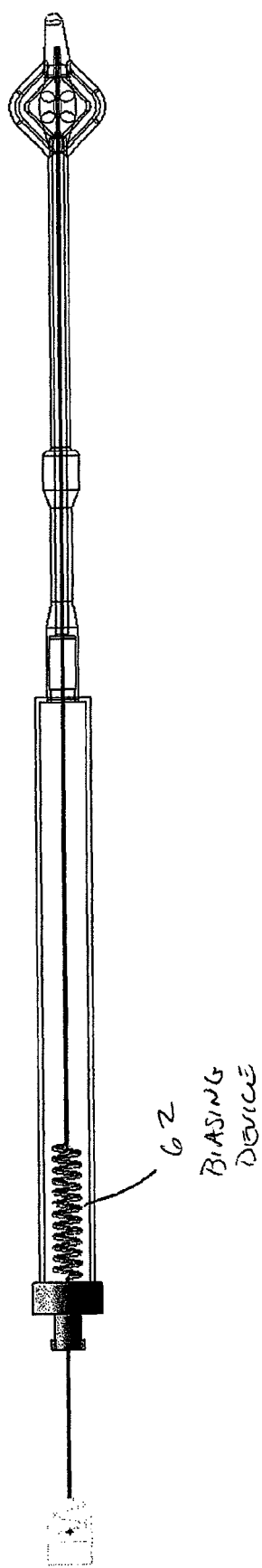
FIG. 15 is a sectional view of the catheter coupled to the installation tool and showing an embodiment of a biasing device.
Figure 16:
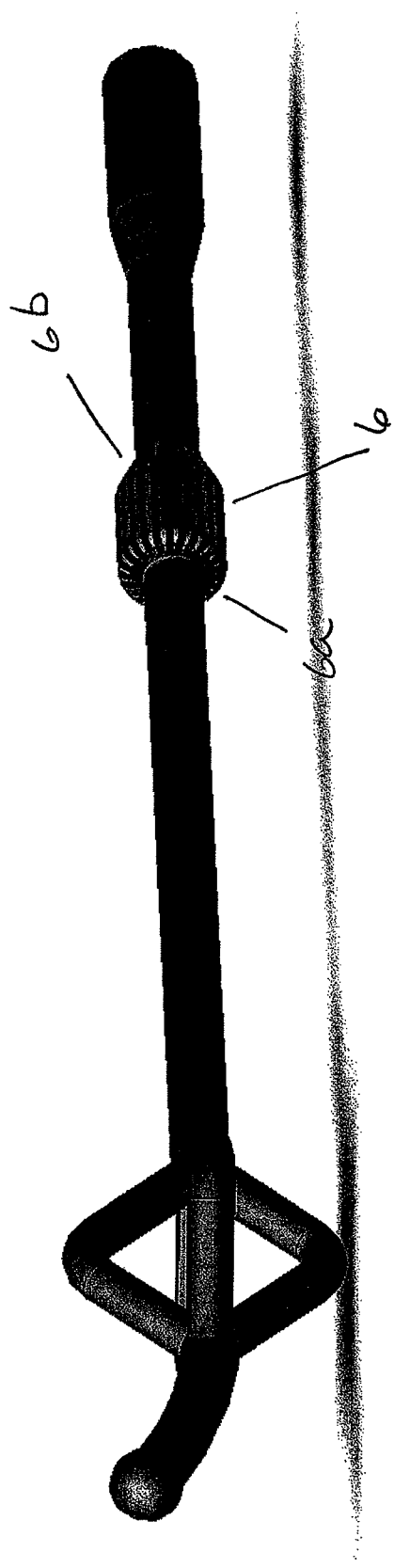
FIG. 16 shows an alternate embodiment of the catheter.
Figure 17:
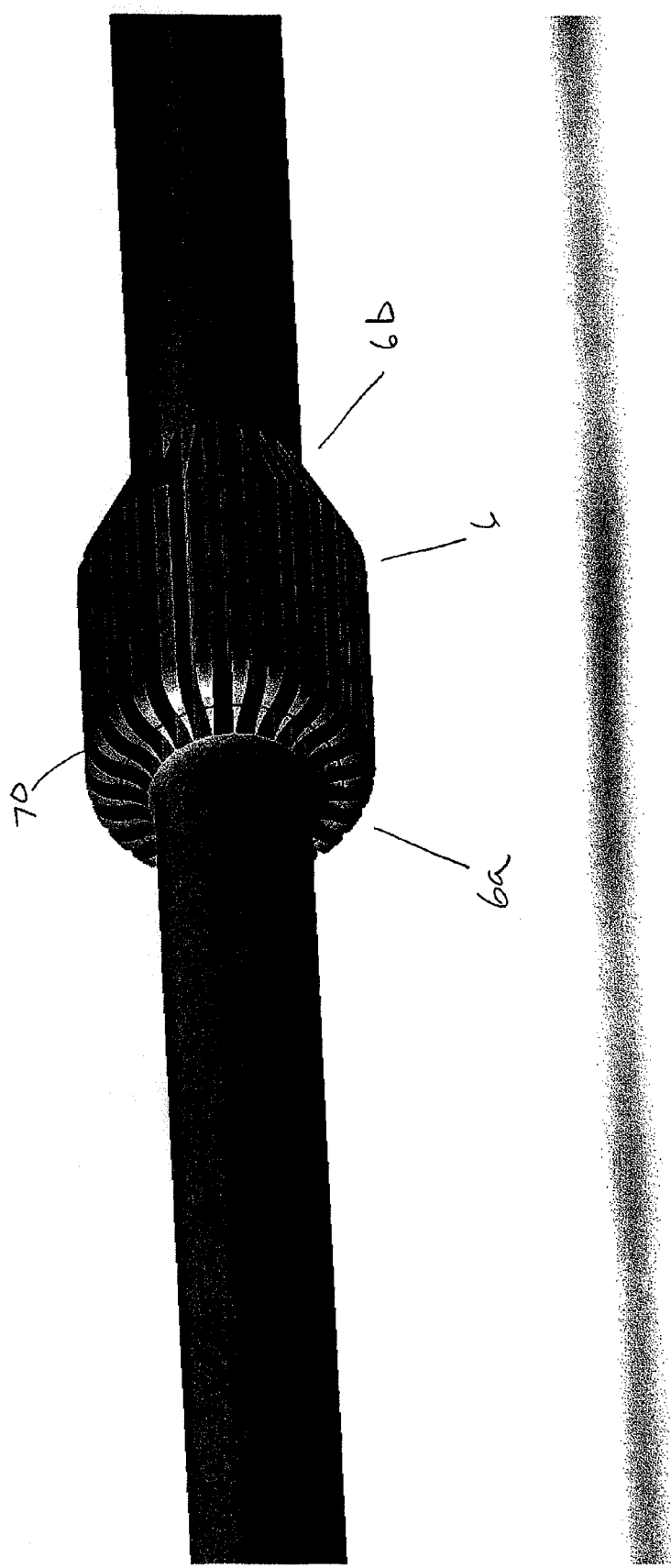
FIG. 17 shows a view of a portion of the catheter.

When catheter 1 is intended for use, for example, as a male urethral catheter, the catheter 1 may be provided with three bulges for anchoring the catheter 1: one bulge against the bladder neck provided by malecot 3 to prevent distal migration, second bulge 6 providing resistance to proximal movement through the external sphincter, and the third bulge 4 to hold the valve 5. Bulges 4 and 6 are spaced from each other along catheter body 2 appropriate for individual patients to provide proper placement of the valve 5. As illustrated in FIGS. 2, 15 and 16, bulge 6 may be a solid structure or alternately formed from a plurality of elements 70. In an unstressed state, the elements 70 extend beyond the wall of a host biological system and deflect to comply with the dimensions of the host system. As such, the deflection of elements 70 places the elements in a stressed state and creates constant tension between said wall and the apparatus. The proximal portion 6a of bulge 6 is shaped to abut, for instance, the external sphincter to prevent proximal movement of the catheter 1. The distal portion 6b of bulge 6 can be any shape that will facilitate distal movement when removal of the catheter is required, for instance a conical shape as shown in FIGS. 15 and 16.

For alternate uses for the catheter, different anchoring structures may be specified.

Figure 4:
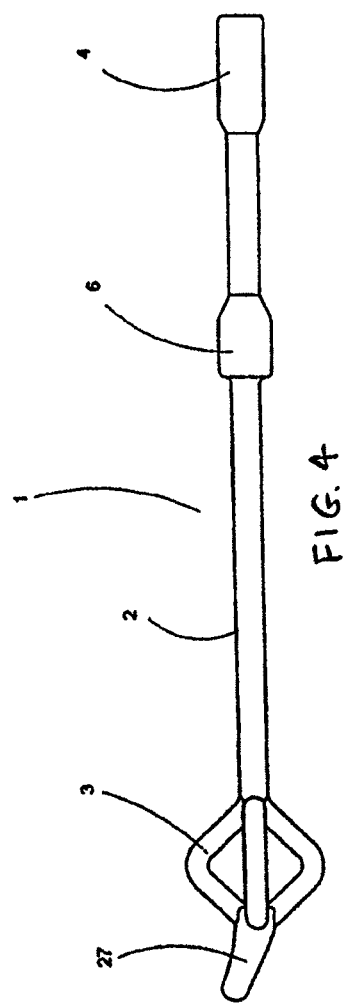
FIG. 4 is a side view of the catheter of FIGS. 1 and 2 with the insertion tool removed.

Although not structurally identical, implanted valved catheter 1 may be similar to that shown in FIG. 3 of incorporated U.S. Pat. No. 6,066,088 using valve 5 as described herein.

From the foregoing description, it will be apparent that there has been provided improved system and method for implanting a catheter having a valve, and particularly an improved system and method for implanting a valved catheter in the urethra, as well as an improved insertion tool and intraurethral valve. Variations and modifications to the herein described system, method, insertion tool, and valve, in accordance with the invention will undoubtedly suggest themselves to those skilled in the art. Accordingly, the foregoing description should be taken as illustrative and not in a limiting sense.

What is claimed is:

1. A system comprising a catheter and a tool for facilitating insertion of the catheter into a lumen, wherein:
   the catheter includes a proximal portion, a distal portion, and an internal channel extending from the catheter proximal portion to the catheter distal portion; and
   the tool includes:
   a distal portion and a proximal portion, and an internal channel extending from the tool distal portion to the tool proximal portion and communicating with the catheter internal channel; and
   an extendible element which includes a distal portion and a proximal portion, and extends from the distal portion of the tool, through the internal channel of the tool into the catheter and the internal channel thereof to the proximal portion of the catheter and which includes an internal channel and has an outer surface, and at least one opening in the proximal portion of the extendible element between the internal channel of the extendible element and the outer surface thereof;
   the system including:
   an extendible element/catheter proximal locking element comprising a member engaged with the proximal portion of the catheter and with the proximal portion of the extendible element and a locking filament slidably disposed within the internal channel of the extendible element from the distal portion to the proximal thereof, exiting the internal channel of the extendible element through the at least one opening, engaging the member engaged with the proximal portion of the catheter, returning to the internal channel of the extendible element and extending to the distal portion of the extendible element so as to releasably attach the extendible element and the proximal portion of the catheter so that the proximal portions of the extendible element and the catheter can be detached; and
   a tool/catheter locking element comprising a member engaged with the proximal portion of the tool and the distal portion of the catheter so as to releasably attach the proximal portion of the tool and the distal portion of the catheter such that one or more of push, pull and rotational forces applied to the tool are transmitted to the catheter distal portion and such that the tool and the catheter can be detached; and
   a handle engaged with the distal portion of the extendible element and the distal portion of the tool which releasably engages the distal portion of the extendible element and the distal portion of the tool, the handle being movable relative to the tool when not engaged therewith;
   wherein:
   when the extendible element is releasably attached to the proximal portion of the catheter and releasably engaged with the distal portion of the tool, with the proximal portion of the tool releasably attached to the distal portion of the catheter, one or more of push, pull and rotational forces applied to the extendible element are transmitted to the proximal and distal portions of the catheter while the catheter is being inserted into the lumen without releasing attachment of the extendible element with the catheter and with the tool; and
   when the extendible element is released from attachment with the proximal portion of the catheter and from engagement with the distal portion of the tool, the extendible element can be axially withdrawn from the catheter.

2. The system of claim 1, wherein the extendible element passes through the tool/catheter locking element, and wherein the tool/catheter locking element includes structure which releasable engages the extendible element and the distal portion of the catheter such that one or more of push, pull and rotational forces applied to the extendible element are transmitted to the distal portion of the catheter.

3. The system according to claim 1, wherein the extendible element and the handle are configured such that when the handle and the distal portion of the tool are releasably engaged, the catheter is in a stressed state.

4. The system according to claim 1, wherein the extendible element and the handle are configured such that when the handle and the distal portion of the tool are not engaged, the catheter is in a relaxed state.

5. The system of claim 1 comprising a valve disposed in the distal portion of the catheter which selectively opens and blocks the internal channel of the catheter.

6. The system according to claim 5 wherein the valve is operable to change a state of the valve in response to an external magnetic field.

7. The system according to claim 5, wherein the valve comprises a valve, a valve passage through the valve in communication with the internal channel of the catheter and a movable valve element which when seated in the valve seat closes the valve passage.

8. The system according to claim 7 wherein the movable valve element comprises a magnet and the valve seat comprises a magnetic material which cooperate to attract and bias the movable valve element into the valve seat to close the valve passage and to move the movable valve element out of the valve seat in response to an external magnetic field to open the valve passage.

9. The system according to claim 7, wherein extendible element passes through the valve and holds the movable valve element out of the valve seat, thereby opening the valve passage.

10. The system according to claim 1, wherein the tool/catheter locking element comprises a tip member which is attached to the proximal portion of the tool and which extends into the distal portion of the catheter and a ring disposed in the distal portion of the catheter proximally of the tip member which releasably engage to releasably couple the tool and the catheter.

11. The system according to claim 10, wherein:
the tip member includes an axial hole and the ring includes an axial hole axially aligned with the hole in the tip member;
the extendible element passes through the aligned holes and causes the tip member and the ring to engage; and
withdrawal of the extendible from the aligned holes causes the tip member and the ring to disengage and release coupling of the proximal portion of the tool and the distal portion of the catheter.

12. The system according to claim 1 wherein the catheter further comprises:
an outside surface; and
at least one structure for preventing migration of the catheter in a lumen, thus anchoring the catheter against undesired axial movement in the lumen.

13. The system according to claim 12, wherein the at least one structure for preventing migration of the catheter is at least one bulge extending outwardly from the outside surface of the catheter.

14. The system according to claim 12, wherein the at least one structure for preventing migration of the catheter is a deflectable spring element extending outwardly from the outside surface of the catheter.

15. The system of claim 1 wherein the member engaged with the proximal portion of the catheter comprises a socket which receives therein an end of the proximal portion of the extendible element, the socket having spaced openings therein through which the locking filament passes before returning to the internal channel of the extendible element.

16. The system according to claim 1, wherein the locking filament has an outer diameter of between approximately 0.002 inches and 0.020 inches.

17. The system according to claim 1, wherein the catheter is a urological catheter adapted to be inserted in a urinary system, the system comprising:
a first structure at the proximal portion of the catheter adapted to fit within a bladder of the urinary system proximal to a bladder neck of the urinary system and arrest distal movement of the catheter when inserted into the urinary system; and
a second structure at the proximal portion of the catheter spaced from the first structure adapted to fit within the bladder neck—and prevent proximal migration of the catheter when inserted into the urinary system.

18. The system according to claim 17 wherein the first structure comprises a malecot.

19. The system according to claim 17 wherein the second structure comprises a bulge.

20. A system comprising a catheter and a tool for facilitating insertion of the catheter into a lumen, wherein:
the catheter includes a proximal portion, a distal portion, and an internal channel extending from the catheter proximal portion to the catheter distal portion; and
the tool includes:
a distal portion and a proximal portion, and an internal channel extending from the tool distal portion to the tool proximal portion and communicating with the catheter internal channel; and
an extendible element which includes a distal portion and a proximal portion, and extends from the distal portion of the tool, through the internal channel of the tool, into the catheter and the internal channel thereof to the proximal portion of the catheter and which includes an internal channel and has an outer surface, and at least one opening in the proximal portion of the extendible element between the internal channel of the extendible element and the outer surface thereof;
the system including:
an extendible element/catheter proximal locking element comprising a member engaged with the proximal portion of the catheter and with the proximal portion of the extendible element and a locking filament slidably disposed within the internal channel of the extendible element from the distal portion to the proximal thereof, exiting the internal channel of the extendible element through the at least one opening, engaging the member engaged with the proximal portion of the catheter, returning to the internal channel of the extendible element and extending to the distal portion of the extendible element so as to releasably attach the extendible element and the proximal portion of the catheter so that the proximal portions of the extendible element and the catheter can be detached; and
a tool/catheter locking element comprising a member engaged with the proximal portion of the tool and the distal portion of the catheter so as to releasably attach the proximal portion of the tool and the distal portion of the catheter such that one or more of push, pull and rotational forces applied to the tool are transmitted to the catheter distal portion and such that the tool and the catheter can be detached; and
a handle engaged with the distal portion of the extendible element and the distal portion of the tool which releasably engages the distal portion of the extendible element and the distal portion of the tool, the handle being movable relative to the tool when not engaged therewith;
wherein:
the extendible element, and the handle and the tool are configured so that movement of the handle relative to the tool towards the proximal portion of the catheter extends the extendible element within the catheter towards the proximal portion of the catheter and axially stresses the catheter, with the handle being releasably engageable with the tool distal portion, and movement of the handle relative to the tool towards the distal portion of the catheter retracts the element within the catheter towards the distal portion of the catheter and relaxes the catheter;
when the extendible element is releasably attached to the proximal portion of the catheter and releasably engaged with the distal portion of the tool, with the proximal portion of the tool releasably attached to the distal portion of the catheter, one or more of push, pull and rotational forces applied to the extendible element are transmitted to the proximal and distal portions of the catheter while the catheter is being inserted into the lumen without releasing attachment of the extendible element with the catheter and with the tool; and
when the extendible element is released from attachment with the proximal portion of the catheter and from engagement with the distal portion of the tool, the extendible element can be axially withdrawn from the catheter.

21. A system comprising a catheter and a tool for facilitating insertion of the catheter into a lumen, wherein:
the catheter includes a proximal portion, a distal portion, an internal channel extending from the catheter proximal portion to the catheter distal portion, and valve disposed in the distal portion of the catheter which selectively opens and blocks the internal channel of the catheter; and the tool includes:
a distal portion, a proximal portion and an internal channel extending from the tool distal portion to the tool proximal portion and communicating with the catheter internal channel via the valve; and
an extendible element which includes a distal portion and a proximal portion, and extends from the distal portion of the tool, through the internal channel of the tool into the catheter, through the valve and into the catheter internal channel to the proximal portion of the catheter and which includes an internal channel and has an outer surface, and at least one opening in the proximal portion of the extendible element between the internal channel of the extendible element and the outer surface thereof;
the system including:
an extendible element/catheter proximal locking element comprising a member engaged with the proximal portion of the catheter and with the proximal portion of the extendible element and a locking filament slidably disposed within the internal channel of the extendible element from the distal portion to the proximal thereof, exiting the internal channel of the extendible element through the at least one opening, engaging the member engaged with the proximal portion of the catheter, returning to the internal channel of the extendible element and extending to the distal portion of the extendible element so as to releasably attach the extendible element and the proximal portion of the catheter so that the proximal portions of the extendible element and the catheter can be detached; and
a tool/catheter locking element comprising a member engaged with the proximal portion of the tool and the distal portion of the catheter so as to releasably attach the proximal portion of the tool and the distal portion of the catheter such that one or more of push, pull and rotational forces applied to the tool are transmitted to the catheter distal portion and such that the tool and the catheter can be detached;
wherein the valve comprises a valve seat, a valve passage through the valve in communication with the internal channel of the catheter and a movable valve element biased to seat in the valve seat and close the valve passage; and
wherein:
the extendible element passes through the valve and holds the valve element out of the valve seat opening the valve passage, and when the extendible element is retracted from the catheter the valve element seats in the valve seat and closes the valve passage;
when the extendible element is releasably attached to the proximal portion of the catheter and releasably engaged with the distal portion of the tool, with the proximal portion of the tool releasably attached to the distal portion of the catheter, one or more of push, pull and rotational forces applied to the extendible element are transmitted to the proximal and distal portions of the catheter while the catheter is being inserted into the lumen without releasing attachment of the extendible element with the catheter and with the tool; and
when the extendible element is released from attachment with the proximal portion of the catheter and from engagement with the distal portion of the tool, the extendible element can be axially withdrawn from the catheter.
22. The system according to claim 21, wherein the movable valve element comprises a magnet and the valve seat comprises a magnetic material which cooperate to attract and bias the movable valve element into the valve seat to close the valve passage and to move the movable valve element out of the valve seat in response to an external magnetic field to open the valve passage.
23. A system comprising a catheter and a tool for facilitating insertion of the catheter into a lumen, wherein:
the catheter includes a proximal portion, a distal portion, and an internal channel extending from the catheter proximal portion to the catheter distal portion; and
the tool includes:
a distal portion and a proximal portion, and an internal channel extending from the tool distal portion to the tool proximal portion and communicating with the catheter internal channel; and
an extendible element which includes a distal portion and a proximal portion, and extends from the distal portion of the tool, through the internal channel of the tool into the catheter and the internal channel thereof to the proximal portion of the catheter;
the system including:
an extendible element/catheter proximal locking element comprising a member engaged with the proximal portion of the catheter and with the proximal portion of the extendible element so as to releasably attach the extendible element and the proximal portion of the catheter so that the proximal portions of the extendible element and the catheter can be detached; and
a tool/catheter locking element comprising a member engaged with the proximal portion of the tool and the distal portion of the catheter so as to releasably attach the proximal portion of the tool and the distal portion of the catheter such that one or more of push, pull and rotational forces applied to the tool are transmitted to the catheter distal portion and such that the tool and the catheter can be detached; and
a handle engaged with the distal portion of the extendible element and the distal portion of the tool which releasably engages the distal portion of the extendible element and the distal portion of the tool, the handle being movable relative to the tool when not engaged therewith;
wherein:
the tool/catheter locking element comprises a tip member which is attached to the proximal portion of the tool and which extends into the distal portion of the catheter and a ring disposed in the distal portion of the catheter proximally of the tip member which releasably engage to releasably couple the tool and the catheter;
the tip member includes an axial hole and the ring includes an axial hole axially aligned with the hole in the tip member;
the extendible element passes through the aligned holes and causes the tip member and the ring to engage; and
withdrawal of the extendible from the aligned holes causes the tip member and the ring to disengage and release coupling of the proximal portion of the tool and the distal portion of the catheter; and
wherein:
when the extendible element is releasably attached to the proximal portion of the catheter and releasably engaged with the distal portion of the tool, with the proximal portion of the tool releasably attached to the distal portion of the catheter, one or more of push, pull and rotational forces applied to the extendible element are transmitted to the proximal and distal portions of the catheter while the catheter is being inserted into the lumen without releasing attachment of the extendible element with the catheter and with the tool; and when the extendible element is released from attachment with the proximal portion of the catheter and from engagement with the distal portion of the tool, the extendible element can be axially withdrawn from the catheter.

\* \* \* \* \*